US006679875B2

(12) United States Patent
Honda et al.

(10) Patent No.: US 6,679,875 B2
(45) Date of Patent: Jan. 20, 2004

(54) MEDICAL TREATMENT SYSTEM

(75) Inventors: Yoshitaka Honda, Tokorozawa (JP);
Tomohisa Sakurai, Sagamihara (JP);
Kazue Tanaka, Sagamihara (JP); Taro Miyazawa, Hino (JP)

(73) Assignee: Olympus Corporation, Tokyo (JP)

( * ) Notice: Subject to any disclaimer, the term of this patent is extended or adjusted under 35 U.S.C. 154(b) by 173 days.

(21) Appl. No.: 10/074,381

(22) Filed: Feb. 12, 2002

(65) Prior Publication Data

US 2002/0115917 A1 Aug. 22, 2002

(30) Foreign Application Priority Data

Feb. 20, 2001 (JP) ......................................... 2001-044094

(51) Int. Cl.[7] .............................................. A61B 17/00
(52) U.S. Cl. .................................. 606/1; 606/34; 606/41
(58) Field of Search ................................ 606/1, 34–39, 606/40

(56) References Cited

U.S. PATENT DOCUMENTS

| 4,931,047 | A |   | 6/1990  | Broadwin et al. |
|-----------|---|---|---------|-----------------|
| 5,300,926 | A | * | 4/1994  | Stoeckl ........................ 345/157 |
| 5,455,766 | A | * | 10/1995 | Scheller et al. ................. 606/4 |
| 5,540,682 | A | * | 7/1996  | Gardner et al. ................ 606/37 |
| 5,609,560 | A |   | 3/1997  | Ichikawa et al. |
| 5,788,688 | A | * | 8/1998  | Bauer et al. .................... 606/1 |
| 5,951,545 | A | * | 9/1999  | Schilling et al. ............... 606/37 |
| 6,117,127 | A | * | 9/2000  | Helmreich et al. ............. 606/1 |

FOREIGN PATENT DOCUMENTS

| JP | 11-318916 | 11/1999 |
| JP | 11-318935 | 11/1999 |

* cited by examiner

Primary Examiner—Roy D. Gibson
(74) Attorney, Agent, or Firm—Scully, Scott, Murphy & Presser

(57) ABSTRACT

A medical treatment system has medical treatment equipment and a control device that controls the operation of this medical treatment equipment. The medical treatment equipment has an operation control section that controls operation of a therapeutic instrument connected to the medical treatment equipment with respect to a selected single function thereof. The control device is constructed including a hand switch and foot switch. This hand switch and foot switch are provided with mode input sections. Also, the foot switch has an operating switch. The control device is constituted by a selection section that recognizes and selects an operating mode of the items of the medical treatment equipment in accordance with an operating mode signal from a mode input section of the hand switch or foot switch, a switchover section that is switched over such that an on/off signal from the operating switch of the foot switch is transmitted to the items of the medical treatment equipment selected by this selection section, and a display data generating section that generates display data for displaying on a monitor, using as an input signal the on/off condition of the operating switch of the foot switch or the operating mode of the item of the medical treatment equipment selected at the selection section.

19 Claims, 11 Drawing Sheets

MEDICAL TREATMENT SYSTEM

This application claims benefit of Japanese application number 2001-044094 filed in Japan on Feb. 20, 2001, the contents of which are incorporated by this reference.

BACKGROUND OF THE INVENTION

1. Field of the Invention

The present invention relates to a medical treatment system wherein the operation etc. of medical equipment is controlled by manipulation of a switch.

2. Description of the Related Art

With the development of medical treatment technology in recent years, a wide range of medical equipment of various types has come into use and the range of functionality of this equipment continues to be expanded. Such medical equipment of various types includes electric scalpel devices, ultrasound operating devices, and laser scalpels etc. of many types. Such medical equipment may be employed on its own or may be employed in the form of a compound medical treatment system. In the case of such medical equipment, the operator treats the lesion etc of the diseased part while holding the scalpel unit in his hand. Turning the output of such medical equipment on or off is therefore frequently performed using a foot switch operated by the foot. In particular, in the case of operations performed under endoscopy, since the operator also manipulates the endoscope using his/her hand, output control is often performed using a foot switch.

Examples of such medical treatment systems are disclosed in Japanese Unexamined Patent Application Publication No. 11-318916 or Japanese Unexamined Patent Application Publication No. 11-318935.

The medical treatment system disclosed in the above Japanese Unexamined Patent Application No. 11-318916 is arranged to be capable of controlling the operation of a plurality of items of medical equipment by switching over a foot switch or hand switch and the like.

This medical treatment system comprises switches that govern the operation of the items of medical equipment provided as the switches such as the aforesaid foot switch or hand switch, a selection switch that selects an operating mode of the items of medical equipment, and display means including operation display means that displays the operating mode of the items of medical equipment and selection operation mode display means that selectively displays the operating mode selected by the aforesaid selection switch.

The operator treats the diseased part of the patient in the operating mode of a desired device in the above medical treatment system. In this medical treatment system, the operating mode of the device desired by the operator is selected by operating the selection switch. In this process, the selection condition of the operating mode of the aforesaid medical treatment system that has been selected is selectively displayed by the selection operation mode display means. In this way, the operator can easily ascertain the selected operation mode.

Thus, in this condition, the operator depresses the operating switch and control operation can be achieved of the device in the aforesaid medical treatment system desired by the operator in the selected operating mode, and in this way treatment of the diseased part of the patient can be effected in the operating mode desired by the operator.

In contrast, in the medical treatment system described in Japanese Unexamined Patent Application Publication No. 11-318935, there are provided a plurality of switches such as hand switches whereby control switchover is achieved of the operating modes of a plurality of items of medical treatment equipment that perform at least one of examination, diagnosis and treatment.

In the above medical treatment systems, it is arranged for operation of the medical treatment equipment to be controlled by selectively switching over the operating mode of the medical treatment equipment by operating a plurality of switches such as the aforesaid hand switch. This medical treatment system comprises switch-operation recognition means for recognizing the switchover operation condition of the switches provided as the aforementioned foot switch or hand switch etc. and display means that displays the results of this switch-operation recognition means.

The operator carries out treatment of the diseased part of the patient in the desired operating mode of the device in the aforesaid medical treatment system. While he/she is doing this, it is arranged for the operator to be able to recognize in a simple manner the current switch operating condition by viewing the display means with the natural line of sight.

However, with the medical treatment system disclosed in the aforementioned Japanese Unexamined Patent Application Publication No. 11-318916, the preparation required for achieving output by the intended items of medical equipment was complicated in that the desired operating mode of the medical equipment could not be set without depressing one by one the selection switches that select an operating mode of the items of medical treatment equipment.

In the medical treatment system disclosed in the aforementioned Japanese Unexamined Patent Application Publication No. 11-318935, switch-operation recognition means (hereinbelow referred to as a foot position sensor) is provided in order to solve the above problem. In the aforementioned medical treatment system, ease of the operation of selecting the operating switch is improved by displaying the result detected by the aforementioned foot position sensor on the display means. However, in the aforementioned medical treatment system, since the respective operating switch is provided in one-to-one correspondence with the aforementioned foot position sensor, it is necessary to provide operating switches equal to the number of selections of operating modes. In the aforementioned medical treatment system, there was therefore the problem that the foot switch employed became of large size.

It should be noted that for example as disclosed in U.S. Pat. No. 4,931,047 medical treatment equipment has been proposed in which suction of living tissue and arrest of hemorrhage are performed by a single item of equipment.

Also, in other proposed medical treatment systems, items of medical equipment are collectively controlled by means of respective ID codes, for example as disclosed in U.S. Pat. No. 5,609,560.

SUMMARY OF THE INVENTION

An object of the present invention is to provide a medical treatment system in which operation of a plurality of items of medical treatment equipment can be achieved in a straightforward fashion and reliably and wherein devices are reduced in size.

A further object of the present invention is to provide a medical treatment system wherein the selection, determination and alteration of operating mode of the various items of medical treatment equipment can be achieved efficiently and without impairing safety and in which efficiency of a medical operation can be improved.

A further object of the present invention is to provide a medical treatment system in which the condition of the various items of medical equipment can be viewed without changing the operator's gaze, whilst looking at the endoscope image.

A further object of the present invention is to provide a medical treatment system in which selection, determination and alteration of operating mode can be achieved without turning the line of sight from the therapeutic instrument and the efficiency of the medical operation can be improved.

A medical treatment system according to the present invention having medical treatment equipment and a control device that controls the operation of this medical treatment equipment comprises: an operation control section that controls operation by a single function wherein a therapeutic instrument connected to said medical treatment equipment is selected; a selection switchover section provided in said control device and that selects a single function in a therapeutic instrument by controlling said operation control section; a selection input section that selectively inputs a single function in a therapeutic instrument by operating said selection switchover section by selection of a prescribed input section from among input sections arranged corresponding to the number of functions possessed by said therapeutic instrument; and an operating switch that outputs operation instructions in respect of a single function in the therapeutic instrument selected by said selective input section to said selection switchover section.

Also, a medical treatment system according to the present invention having medical treatment equipment and a control device that controls the operation of this medical treatment equipment comprises: an operation control section that controls operation by a single function wherein a therapeutic instrument connected to said medical treatment equipment is selected; a selection switchover section provided in said control device and that selects a single function in a therapeutic instrument by controlling said operation control section; a selection input section that selectively inputs a single function in a therapeutic instrument by operating said selection switchover section by selection of a prescribed input section from among input sections arranged corresponding to the number of functions possessed by said therapeutic instrument; a switchover section that, when there are a plurality of items of said medical treatment equipment, selects a corresponding item of medical treatment equipment from among said plurality of items of medical treatment equipment in accordance with a single function in the therapeutic instrument selected by said selection switchover section; and an operating switch that outputs operation instructions in respect of a single function in the therapeutic instrument selected by said selective input section to said selection switchover section.

Other features and advantages of the present invention will be fully clarified by the following description.

DESCRIPTION OF THE PREFERRED EMBODIMENTS

Figure 1:
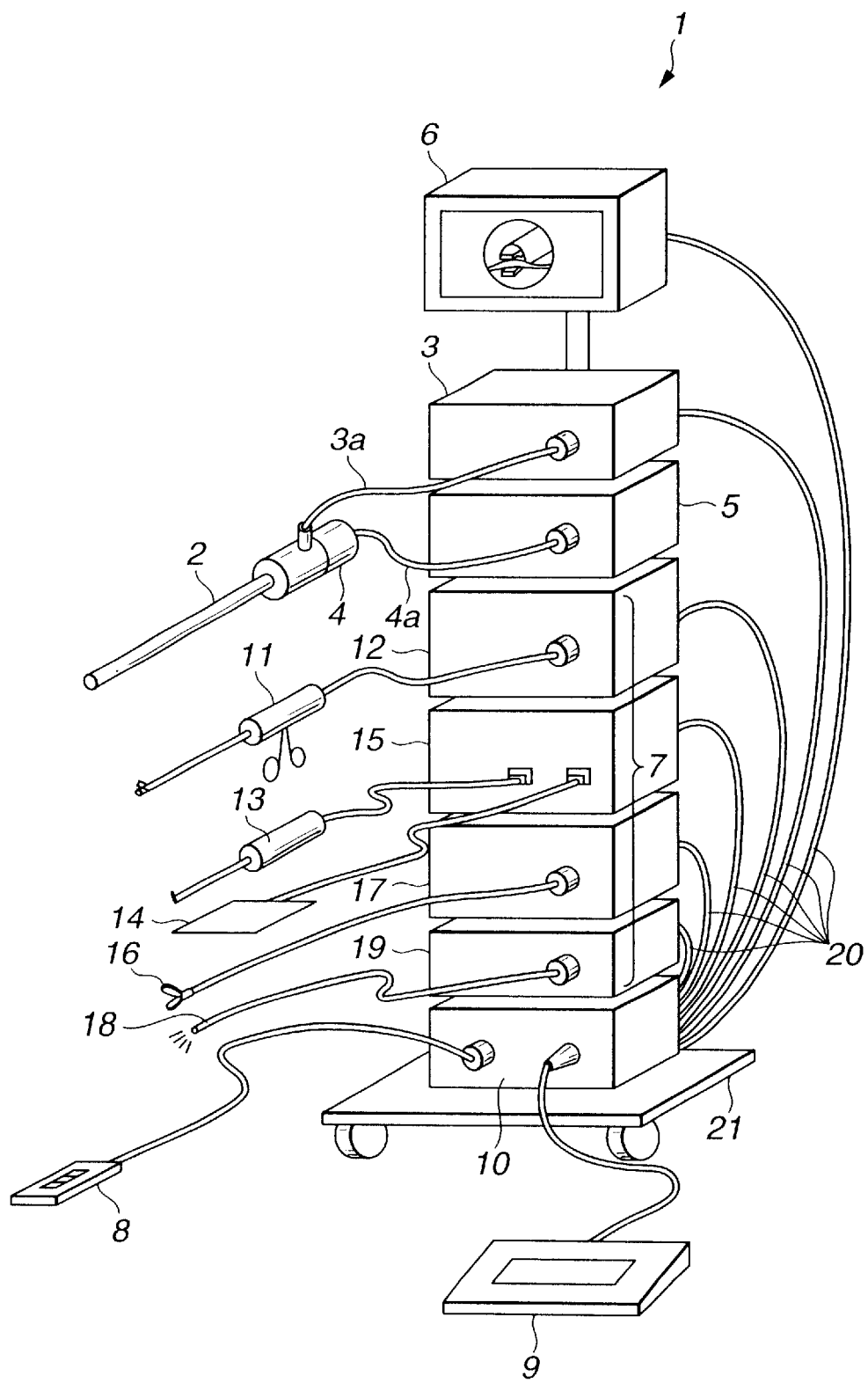
FIG. 1 is an overall layout diagram illustrating the overall layout of a medical treatment system according to a first embodiment of the present invention.

Embodiments of the present invention are described below with reference to the drawings.

In this embodiment, the present invention is applied to a medical treatment system for surgery under endoscopy.

The medical treatment system 1 of the first embodiment of the present invention illustrated in FIG. 1 comprises: an endoscope 2 for observing the interior of body cavities of the patient; a light source device 3 that supplies illuminating light through a light guide cable 3a to the endoscope 2; an endoscope TV camera (hereinbelow called "TV camera") 4 incorporating an image pickup device that picks up the image of the subject obtained by this endoscope 2 and which is mounted on the endoscope 2; an image processor 5 that performs signal processing in respect of the image pickup device through a camera cable 4a of this TV camera 4; a monitor 6 that displays an endoscope image after signal processing by this image processor 5; a plurality of items of medical treatment equipment 7 that perform treatment of a diseased part of the patient; and a medical treatment system control device (hereinbelow "control device") 10 including a hand switch 8 manipulated by the hand and a foot switch 9 manipulated by the foot for giving instructions for selection of this plurality of items of medical treatment equipment 7 or for actuating a prescribed operating mode thereof.

The plurality of items of the medical treatment equipment 7 comprise an ultrasound therapeutic instrument 11 for coagulation/incision treatment of a diseased part using ultrasound vibrations; an ultrasound wave power supply 12 that supplies energy for generating ultrasound vibrations in this ultrasound therapeutic instrument 11 and that controls this ultrasound therapeutic instrument 11; a high frequency therapeutic instrument 13 that performs coagulation/incision treatment by passing high-frequency electric current to the diseased part; a patient counter electrode plate 14 whereby the high frequency current is recovered from this high frequency therapeutic instrument 13; a high-frequency power supply 15 that supplies high frequency current to this high frequency therapeutic instrument 13 and patient counter electrode plate 14 and controls this high frequency therapeutic instrument 13 and patient counter electrode plate 14; a heat therapeutic instrument 16 that performs coagulation treatment of the diseased part using heat; a heat treatment power supply 17 that supplies energy for generating heat in this heat therapeutic instrument 16 and that controls this heat therapeutic instrument 16; a laser therapeutic instrument 18 that performs coagulation treatment by irradiating the diseased part with optical energy; and a laser power supply 19 that supplies optical energy to this laser therapeutic instrument 18 and that controls this laser therapeutic instrument 18.

The outputs of the items of the medical treatment equipment 7, namely, monitor 6, image processor 5, light source device 4, ultrasound power supply 12, high-frequency power supply 15, heat treatment power supply 17 and laser power supply 19 are controlled by connection with the control device 10 through communication cables 20. The monitor 6, image processor 5, light source device 4, ultrasound power supply 12, high-frequency power supply 15, heat treatment power supply 17, laser power supply 19 and control device 10 are made to be moveable by being carried on a cart 21.

Figure 2:
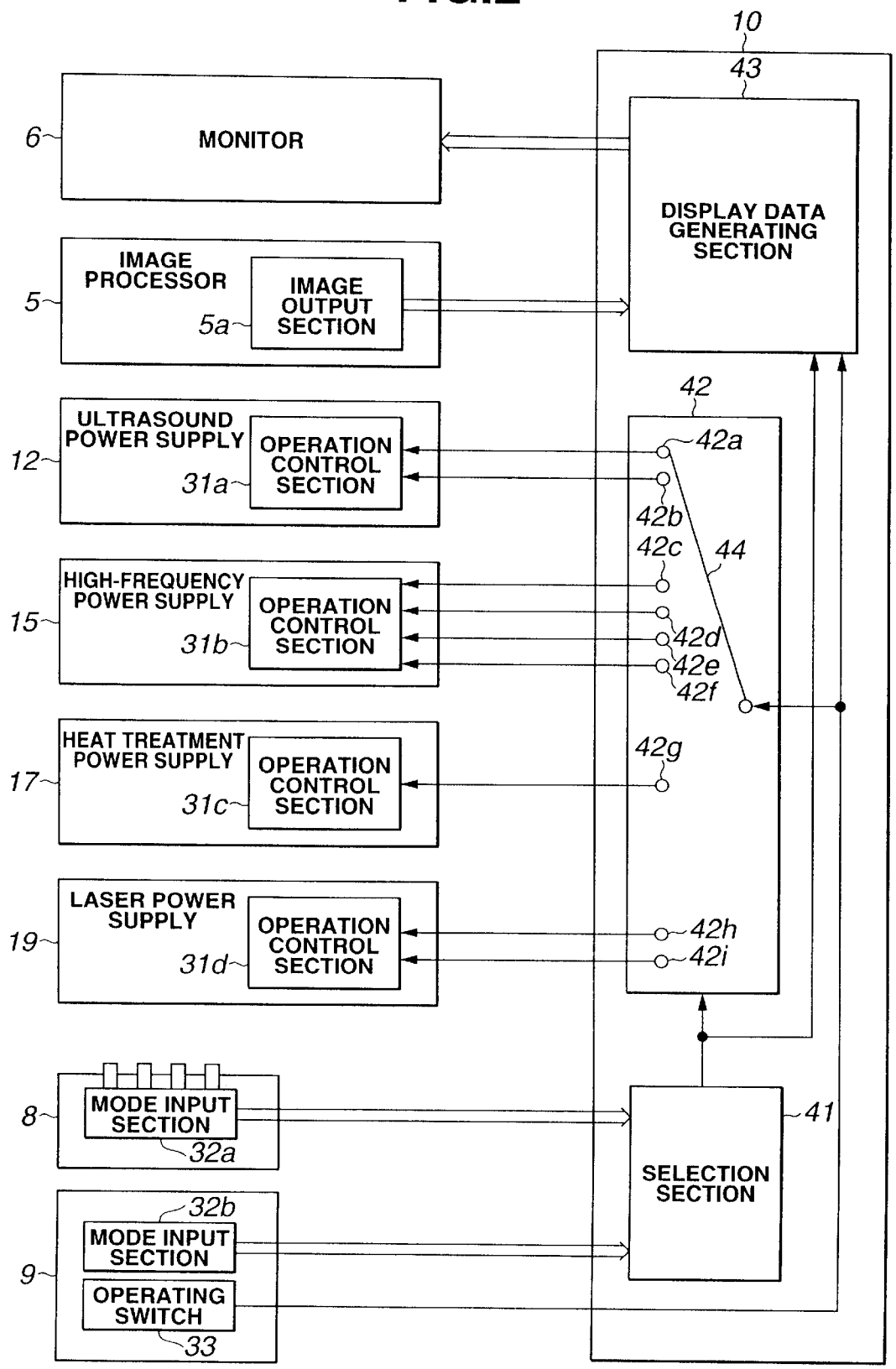
FIG. 2 is a circuit block diagram illustrating the communication connections of the various items of medical treatment equipment of FIG. 1 and the internal layout of a control device.

The plurality of items of the medical treatment equipment 7 and the control device 10 have communication connections arranged as shown in FIG. 2.

The image processor 5 is provided with a signal processing section, not shown, that performs signal processing of the image pickup signal that is output from the TV camera 4 and an image output section 5a is provided for displaying the image that has been subjected to the signal processing by this signal processing section on monitor 6.

The signal that is output from this image output section 5a is output to the monitor 6 through the control device 10 and is displayed as an endoscope image.

The ultrasound power supply 12, high-frequency power supply 15, heat treatment power supply 17 and laser power supply 19 that are connected to the control device 10 are provided with an operation control unit that controls operation of the respective therapeutic instrument and that inputs respective operating mode on/off signals sent from the control device 10, respectively.

Specifically, the ultrasound power supply 12 is provided with an operation control section 31a that controls the operation of ultrasound therapeutic instrument 11 by inputting respective on/off signals of two operating modes, namely, a maximum output mode of the supplied energy and a set output mode.

The high-frequency power source 15 is provided with an operation control section 31b that controls operation of the high frequency therapeutic instrument 13 by inputting respective on/off signals of four operating modes of the supplied high-frequency current, namely, incision mode, coagulation mode, mixing mode and spray mode.

The laser power supply 19 is provided with an operation control section 31c that controls operation of the laser therapeutic instrument 18 by inputting respective on/off signals of two operating modes, namely, continuous mode and intermittent mode of supplied optical energy.

Heat treatment power supply 11 is provided with an operation control section 31d for controlling operation of the heat therapeutic instrument 16 by inputting an on/off signal of supplied energy output.

The hand switch 8 and foot switch 9 are provided with mode input sections for selective input of respective operation modes of the plurality of items of the medical treatment equipment 7.

Specifically, the hand switch 8 is provided with mode input sections 32a. These mode input sections 32a may themselves be for example switches.

The foot switch 9 is provided with mode input sections 32b. These mode input sections 32a, 32b are arranged to output a selected operating mode signal to the control device 10, with selection being performed by detecting the respective operating mode to be selected.

Also, the foot switch 9 comprises one operating switch 33 for performing actual output in respect of the selected operating mode. This operating switch 33 is arranged to output an on/off signal to the control device 10.

The control device 10 comprises a selection section 41 that recognizes and selects the operating mode of the various items of the medical treatment equipment 7 in accordance with the operating mode signal from the mode input sections 32a of the hand switch 8 or from the mode input sections 32b of the foot switch 9; a switchover section 42 that effects switchover such that the on/off signal from the operating switch 33 of the foot switch 9 is transmitted to each of the items of the medical treatment equipment 7 selected by this selection section 41; and a display data generating section 43 that generates display data for displaying on the monitor 6, using as input signal the operating mode of each of the items of the medical treatment equipment 7 selected by the selection section 41 and/or the on/off condition of the operating switch 33 of the foot switch 9.

It should be noted that, for example in the case of this embodiment, the display data generating section 43 may be a superimposer that effects superimposition in accordance with an input signal in the vicinity of the endoscope image that is output from the image processor 5.

The selection section 41 recognizes the operating mode signal when an operating mode signal is input from a mode input section 32a of the hand switch 8 or from a mode input section 32b of the foot switch 9. The selection section 41 also outputs a selection signal for selecting an operating mode of the medical treatment equipment 7 to the switchover section 42 and display data generating section 43.

The switchover section 42 is arranged such that switch 44 is switched over with respect to operating mode contacts 42a to 42i of the selected items of the medical treatment equipment 7 in accordance with the selection signal when this selection signal of the selection section 41 is input thereto.

Also, the switchover section 42 is arranged to transmit an on/off signal to the item of the medical treatment equipment 7 through whichever of the operating mode contacts 42a to 42i has been selected from a switch 44 that is thus switched over, when an on/off signal is input thereto from the operating switch 33 of the hand switch 8.

When a selection signal of the selection section 41 is input thereto, the display data generating section 43 generates display data based on this selection signal for displaying characters indicating the operating mode of the selected item of the medical treatment equipment 7 in the vicinity of the endoscope image and causes these to be displayed on the monitor 6.

Also, the display data generating section 43 is arranged to display on monitor 6 the on/off condition of the operating mode of the selected item of the medical treatment equipment 7 in accordance with the on/off signal when this on/off signal is input from operating switch 33 of the foot switch 9.

In this embodiment, as will be described, the display data generating section 43 indicates the selected condition of the operating mode by flashing the characters displayed on the monitor 6 and indicates the on/off condition of the operating mode by illuminating these characters displayed on the monitor 6.

Next, the detailed construction of the foot switch 9 will be described using FIG. 3 and FIG. 4.

Figure 3:
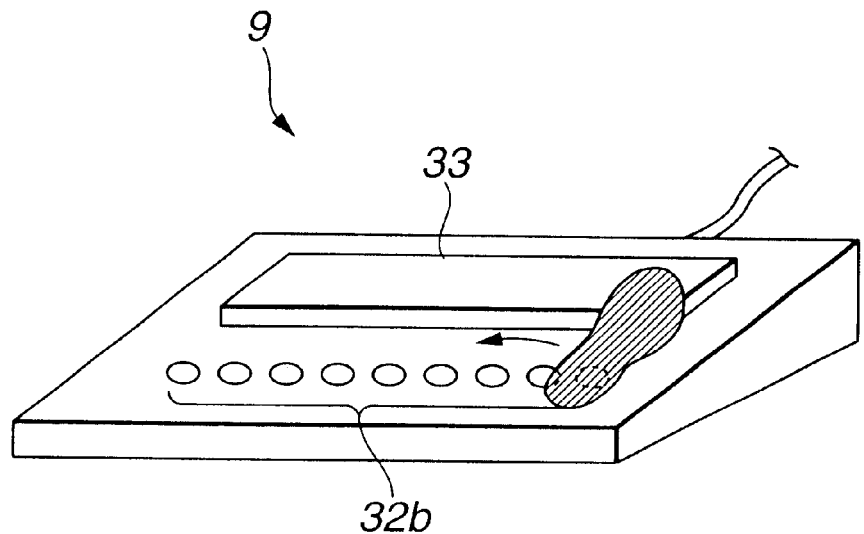
FIG. 3 is an external view illustrating the foot switch of FIG. 2.

As shown in FIG. 3, the foot switch 9 is constituted of a single operating switch 33 and mode input sections 32b arranged corresponding to the number of operating modes of the plurality of items of the medical treatment equipment 7 at the front end face of this operating switch 33.

Figure 4:
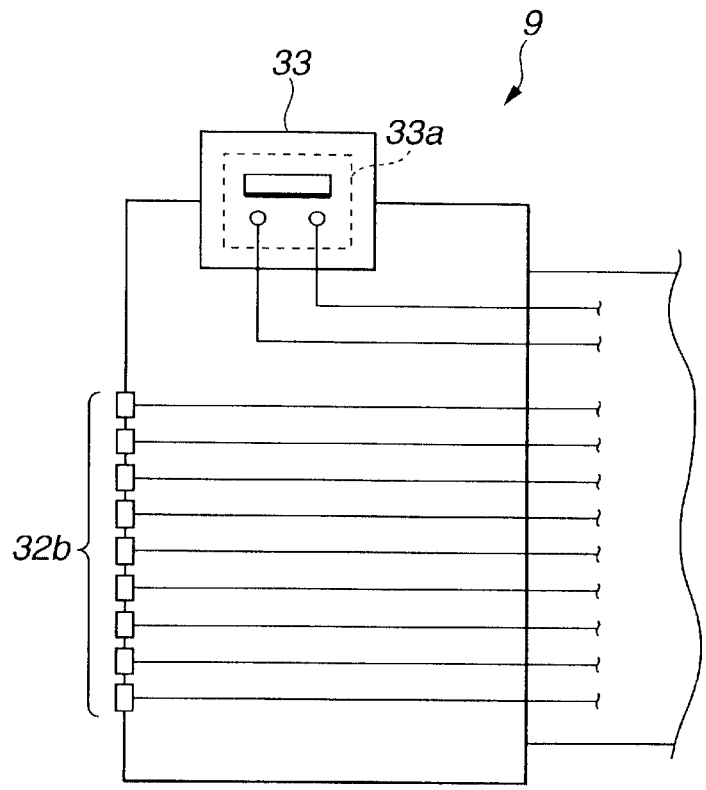
FIG. 4 is a circuit block diagram illustrating the internal layout of the foot switch of FIG. 3.

As shown in FIG. 4, the operating switch 33 is constituted by a contact switch 33a and is arranged such that the on/off signal produced by depression of this contact switch 33a is transmitted to the control device 10.

The mode input sections 32b are constituted by for example infrared sensors. The mode input sections 32b are arranged to be capable of selecting the operating mode in accordance with which of the mode input sections 32b is covered by part of the foot when the operating switch 33 is depressed. Also, the mode input sections 32b are arranged to perform selection by detecting the selected operating mode and outputting an operating mode signal to the control device 10.

The operation of a medical treatment system 1 constructed in this way will now be described.

The surgeon sets up the connection condition as in FIG. 1 by connecting the various items of the medical treatment equipment 7 to the control device 10 and turns the power supply on. When this is done, a subject image obtained by the endoscope 2 is picked up by the image pickup device incorporated in the TV camera 4. This image pickup signal from the image pickup device is subjected to signal processing at the signal processing section of the image processor 5 and output to the monitor 6 from the image output section 5a of this image processor 5 via the display data generating section 43 of the control device 10. The endoscope image is then displayed in the middle of the display screen of the monitor 6. It should be noted that, in this initial condition, since no medical treatment equipment 7 has yet been selected, the condition is one in which only the endoscope image is displayed.

The surgeon then performs treatment on the diseased part of the patient using a desired item of the medical treatment equipment 7. At this point, it will be assumed for example that the surgeon holds the ultrasound therapeutic instrument 11 with one hand or both hands, and performs ultrasound treatment of the diseased part. The surgeon selects for example the maximum output mode of ultrasound therapeutic instrument 11 by depressing the mode input section 32a of the hand switch 8 or by covering the mode input section 32b of the foot switch 9 with part of his foot.

When this is done, as shown in FIG. 2, the mode input section 32a of the hand switch 8 or the mode input section 32b of the foot switch 9 makes a selection by detecting the selected operating mode and outputs the maximum output mode signal of the ultrasound therapeutic instrument 11 to the selection section 41 of the control device 10.

The selection section 41 of the control device 10 recognizes the maximum output mode signal from the mode input section 32a of the hand switch 8 or from mode input section 32b of the foot switch 9 and thereby selects the maximum output mode of the ultrasound therapeutic instrument 11 and outputs a selection signal to the switchover section 42 of the control device 10 and to display the data generating section 43.

The switchover section 42 of the control device 10 switches over a switch 44 to an operating mode contact 42a in accordance with this selection signal. Also, the display data generating section 43 of the control device 10 generates display data indicating maximum output mode of the selected ultrasound therapeutic instrument 11 in accordance with the selection signal from selection section 41 of the control device 10 and causes this to be displayed on the monitor 6 as shown in FIG. 5A.

Figure 5A:
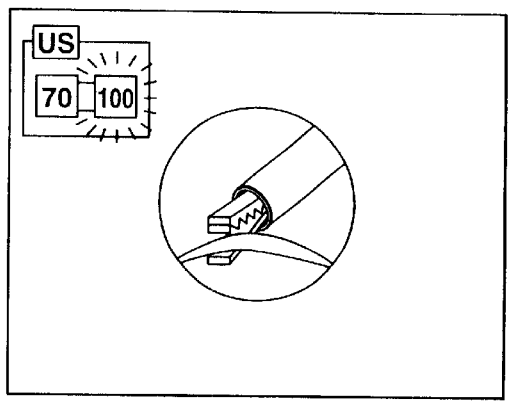
FIG. 5A is an example display of the monitor when the maximum output mode of the endoscope image and of the ultrasound therapeutic instrument is displayed.

As shown in FIG. 5A, the endoscope image is displayed in the middle of the screen of the monitor 6 and characters indicating the operating mode of the ultrasound therapeutic instrument 11 are displayed in the top left-hand corner of the screen of the monitor 6. Specifically, regarding the characters shown in FIG. 5A, in addition to the characters "US" indicating the ultrasound therapeutic instrument 11, the two operating modes: maximum: output mode "100" and set output mode "70" are displayed and the maximum output mode "100", which is selected, is flashed.

The surgeon then commences output to the ultrasound therapeutic instrument 11 by depressing the operating switch 33 of the foot switch 9 using his/her foot. When this is done, the operating switch 33 of the foot switch 9 outputs an ON signal to the switchover section 42 and to the display data generating section 43 of the control device 10.

The switchover section 42 of the control device 10 sends the ON signal to the ultrasound power supply 12 through operating mode contact 42a from switch 44 which has thus been changed over.

The ultrasound power supply 12 receives the ON signal at the operating control section 31a through the operating mode contact 42a. In accordance with the ON signal, the operating control section 31a then performs drive control such that the ultrasound power supply 12 drives the ultrasound therapeutic instrument 11 in the maximum output mode.

Also, the display data generating section 43 of the control device 10, in response to the ON signal, displays the maximum output mode "100" which is flashing as mentioned above on the monitor 6 in an illuminated manner.

In order to stop or interrupt ultrasound treatment of the diseased part, the surgeon then removes his/her foot from the foot switch 9. When this happens, the operating switch 33 of the foot switch 9 outputs an OFF signal to the switchover section 42 and display the data generating section 43 of the control device 10.

The switchover section 42 of the control device 10 sends the OFF signal to the ultrasound power supply 12 through the operating mode contact 42a.

The ultrasound power supply 12 receives the OFF signal in the operating control section 31a through the operating mode contact 42a. The operation control section 31a of the ultrasound power supply 12 then stops output to the ultrasound therapeutic instrument 11 in accordance with the OFF signal.

Also, the display data generating section 43 of the control device 10, in response to the OFF signal, stops display of the characters that are being displayed. When ultrasound treatment is to be performed, the operation described above is again repeated.

Figure 5B:
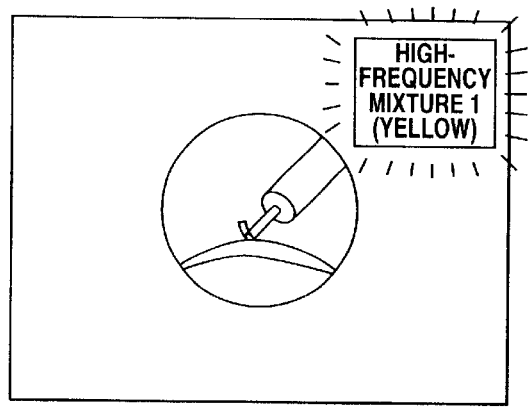
FIG. 5B is an example display of the monitor when the endoscope image and mixed mode of the high frequency therapeutic instrument are displayed.
Figure 5C:
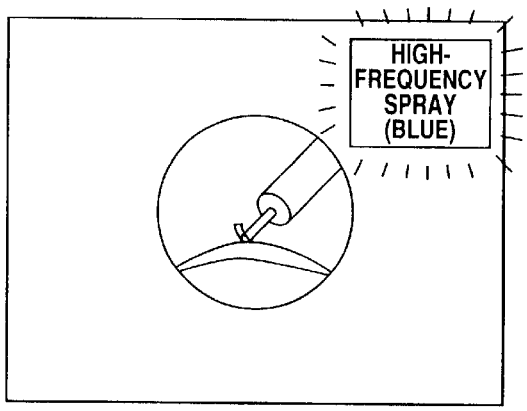
FIG. 5C is an example display of the monitor when the endoscope image and spray mode of the high frequency therapeutic instrument are displayed.

Also, when high frequency treatment of the diseased part is performed, the operation of the control device 10 is identical with that in the case of ultrasound treatment. As the display of the monitor 6, in addition to letters indicating "high-frequency" in the upper right-hand corner of the screen of the monitor 6 as shown in FIG. 5B and FIG. 5C, the operation mode such as "mixed" mode or "spray" mode is displayed for example. It is arranged for the characters shown in this FIG. 5B and FIG. 5C to be displayed for example in yellow or blue color.

Figure 5D:
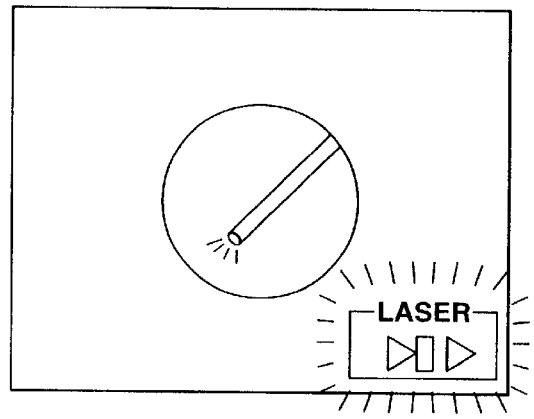
FIG. 5D is an example display of the monitor when the endoscope image and intermittent mode of the laser therapeutic instrument are displayed.

Also, the operation of the control device 10 when laser treatment of the diseased part is performed is identical with that in the case of ultrasound treatment. As to the display of the monitor 6, as shown in FIG. 5D, in addition to letters indicating "LASER", symbols indicating the operating mode such as for example intermittent mode are displayed in the bottom right-hand corner of the screen of the monitor 6.

Also, the control device 10 is arranged to flash the aforementioned characters when an operating mode is selected and to illuminate them during output. The display position of the characters on the screen of the monitor 6 illustrated in FIG. 5A to FIG. 5D can be altered for each item of the medical treatment equipment 7.

As a result, with the medical treatment system 1, by displaying the result selected by the monitor input section 32a provided in the hand switch 8 or by the monitor input section 32b provided in the foot switch 9 on the monitor 6, the condition of the various items of the medical treatment equipment 7 selected and output can be viewed, without turning the line of sight, whilst looking at the endoscope image.

In this way, with the medical treatment system 1 of this first embodiment, the efficiency of surgical operations can be improved since the selection, determination and alteration of operating mode of the various items of the medical treatment equipment 7 can be achieved efficiently and without impairing safety. Also, with the medical treatment system 1 of this first embodiment, the foot switch 9 can be made smaller than conventional ones, since a construction is adopted wherein only a single operating switch 33 is provided in the foot switch 9.

Figure 6:
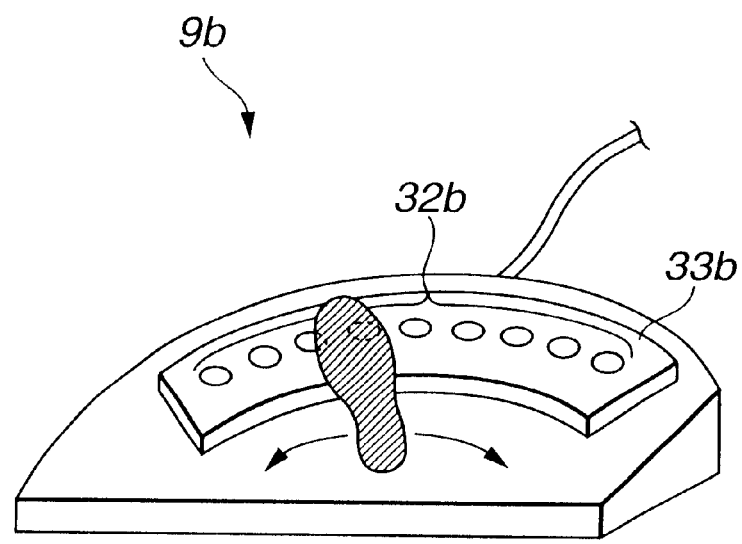
FIG. 6 is an external view of a foot switch illustrating a modified example of FIG. 3.
Figure 7:
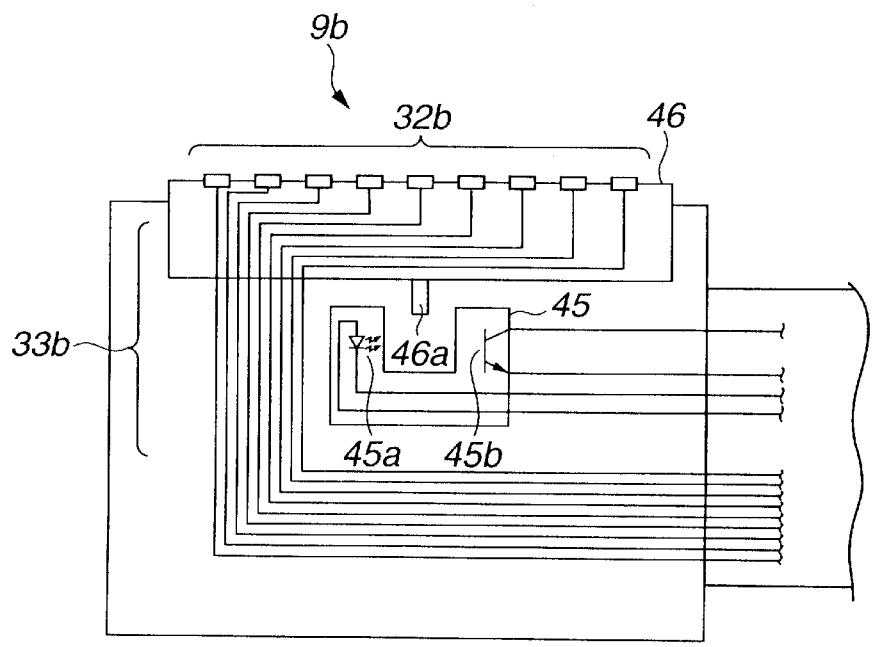
FIG. 7 is a circuit block diagram illustrating the internal layout of the foot switch of FIG. 6.

It should be noted that the foot switch 9 described with reference to FIG. 3 and FIG. 4 could be constructed as shown in FIG. 6 and FIG. 7.

As shown in FIG. 6, in the foot switch 9b, an operating switch 33b is formed in a fan shape and the mode input sections 32b such as an infra-red sensor like that of the foot switch 9 described with reference to FIG. 3 and FIG. 4 are arranged within this operating switch 33b. The foot switch 9b is arranged to perform selection of operating mode of each item of the medical treatment equipment 7 by rotational movement of the foot.

As shown in FIG. 7, the operating switch 33b is constituted by a photocoupler 45. In the operating switch 33b, a threshold section 46a is provided in the middle of the lower section of a switch depression section 46. In the operating switch 33b, a photoswitch type of arrangement is achieved by the threshold section 46a providing screening between an LED 45a and a phototransistor 45b of the photocoupler 45 when this is operated by being depressed. When the operating switch 33b is OFF, the light emitted by the LED 45a is arranged to be always received by the phototransistor 45b.

In this way, since in the foot switch 9b the mode input sections 32b and operating switch 33b are constituted by optical means that has no contact arrangement, even if an anti-explosive construction characteristic of a foot switch is required, a construction can be achieved in which there is no possibility of sparks which could cause ignition being generated.

Figure 8:
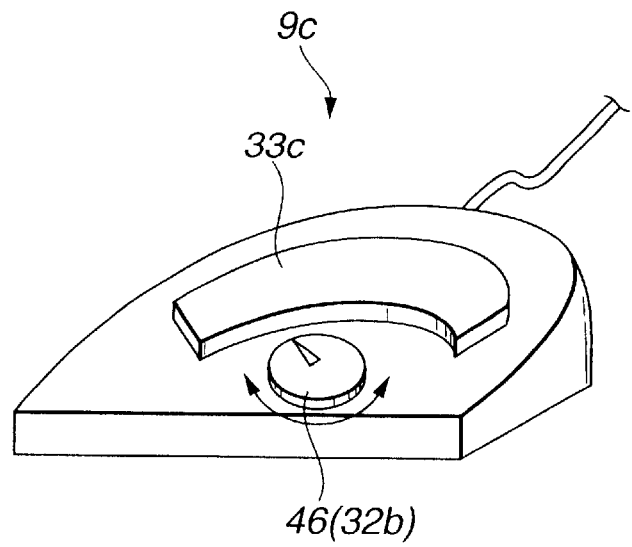
FIG. 8 is an external view of a foot switch illustrating another modified example of FIG. 3.
Figure 9:
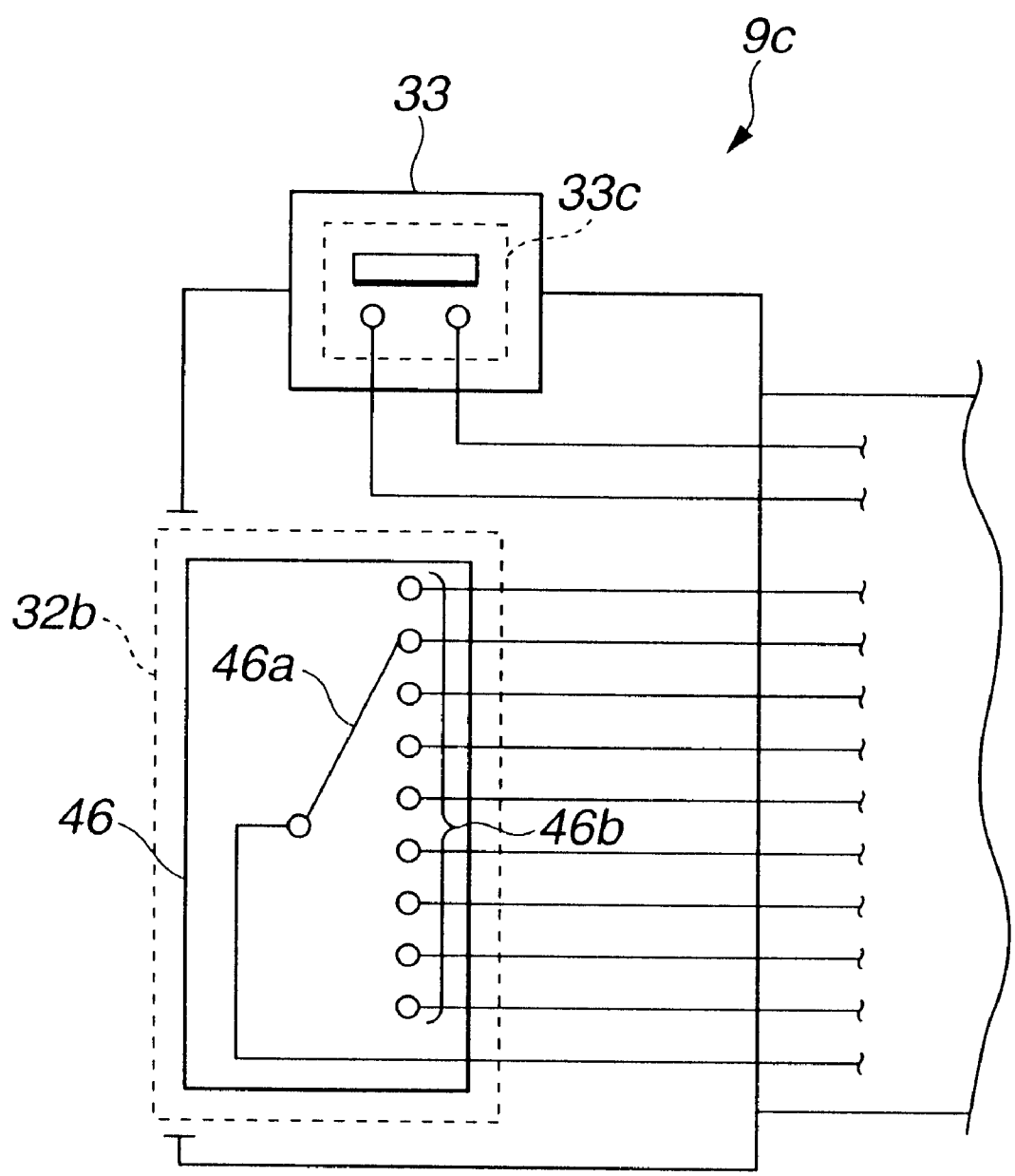
FIG. 9 is a circuit block diagram illustrating the internal layout of the foot switch of FIG. 8.

Also, the foot switch 9 may be constructed as shown in FIG. 8 and FIG. 9.

As shown in FIG. 8, in a foot switch 9c, an operating switch 33c is formed in a fan shape and the mode input sections 32b are constituted by a rotary switch 46.

As shown in FIG. 9, the rotary switch 46, by free rotation of a switch 46a, achieves switch action in which it conducts by contacting one or other of control device side terminals 46b provided in correspondence with the number of operating modes of the items of the medical treatment equipment 7.

In this way, the same operation of the foot switch 9c as of the foot switch 9b described above can be achieved by freely rotating the heel on the rotary switch 29. In this way, in addition to the benefits of the foot switch 9b above, with the foot switch 9c, the same benefits can be achieved inexpensively by using the rotary switch 46 for the mode input sections 32b.

Figure 10:
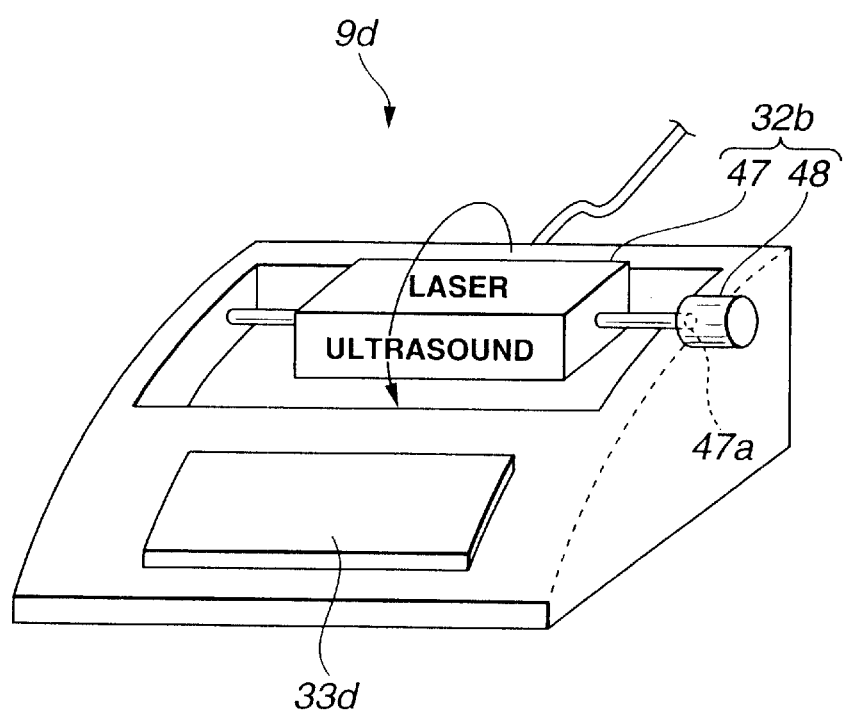
FIG. 10 is an external view of a foot switch illustrating yet another modified example of FIG. 3.

Also, the foot switch 9 may be constructed as shown in FIG. 10.

As shown in FIG. 10, in a foot switch 9d, mode input sections 32b are constituted by a display rotor 47 having a rotary shaft 47a and a rotary switch 48.

In the foot switch 9d the display of the operating mode of the item of the medical treatment equipment 7 in question is altered by freely rotating the display rotor 47 and a switching action is achieved in which it conducts by contacting one or other of control device side terminals, not shown, in the same way as described with reference to the foot switch 9c, using as the switch rotary shaft 47a which is operated by rotating it.

In this way, the foot switch 9d makes possible switchover of operating mode of the medical treatment equipment 7. It should be noted that, although in the drawing the display rotor 47 is of rectangular shape, it could be formed of practically polygonal prismatic shape having curved sidefaces. In this way, in addition to the benefits of the foot switch 9c, the foot switch 9d can achieve the selection effect of the operating switch 33 even by means of the foot switch 9 itself, by employing the display rotor 47 for the mode input sections 32b.

(Second embodiment)

FIG. 11 to FIG. 15 are views relating to a second embodiment of the present invention.

Whereas in the first embodiment the present invention was applied to a medical treatment system for surgery under endoscopy, in the second embodiment the present invention is applied to a medical treatment system in surgery in general. Other than this, the construction is identical with that of the first embodiment, so in the description the same reference symbols are attached to identical structures and further description thereof is omitted.

Figure 11:
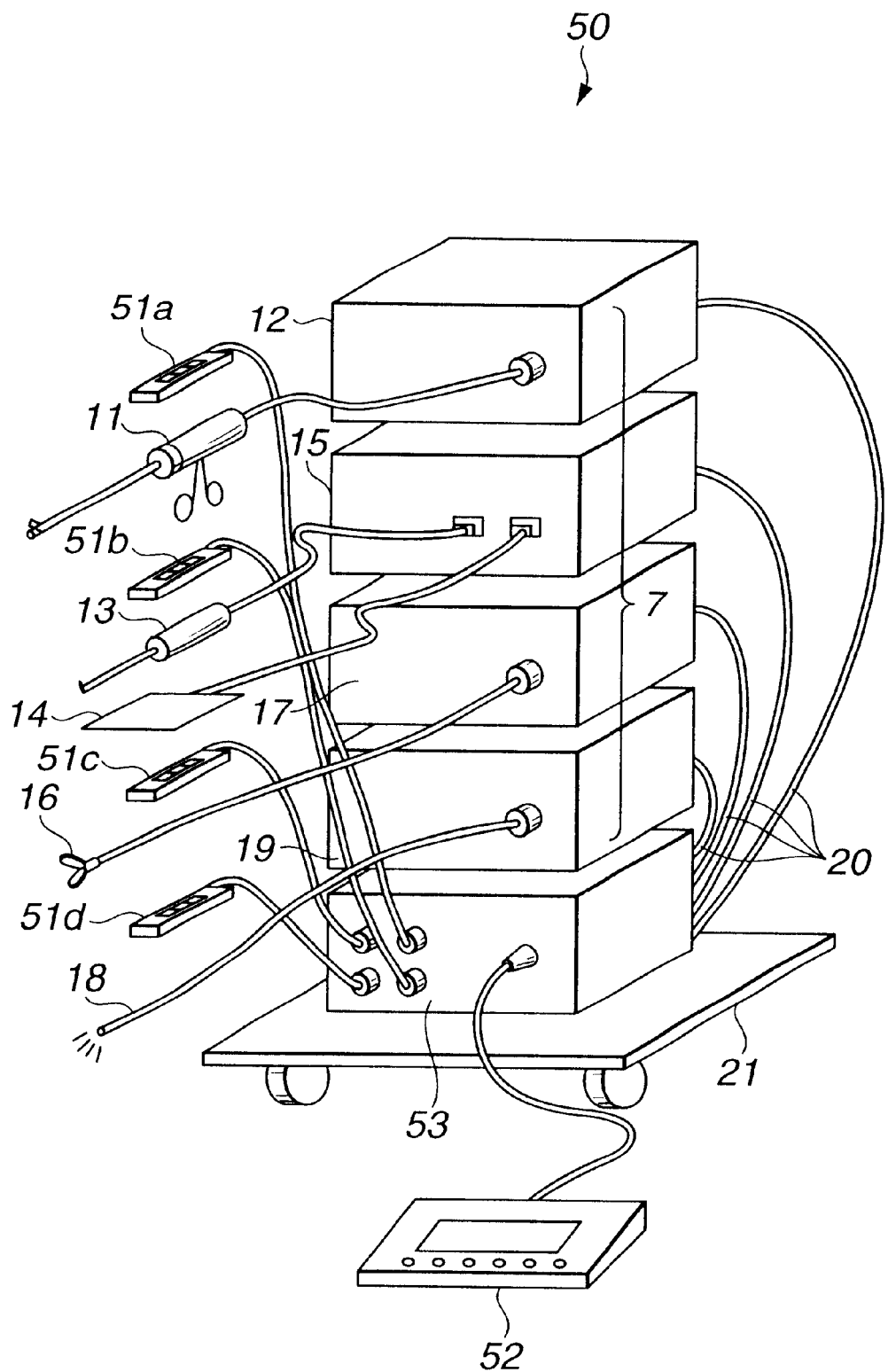
FIG. 11 is an overall layout diagram illustrating the overall layout of a medical treatment system according to a second embodiment of the present invention.

As shown in FIG. 11, a medical treatment system 50 of the second embodiment comprises a plurality of items of the medical treatment equipment 7 just as described in the first embodiment; hand switches 51 (51a to 51d), such as for example a hand switch 51a for the ultrasound therapeutic instrument, a hand switch 51b for the high-frequency therapeutic instrument, a hand switch 51c for the heat therapeutic instrument and a hand switch 51d for the laser therapeutic instrument, that perform control operation of this plurality of items of the medical treatment equipment 7 are freely releaseably mounted on the ultrasound therapeutic instrument 11, high-frequency therapeutic instrument 13, heat therapeutic instrument 16 and laser therapeutic instrument 18, which constitute the therapeutic instrument of the various items of the medical treatment equipment 7. It should be noted that, in this second embodiment, since this is a medical treatment system for surgery in general rather than a medical treatment system for surgery under endoscopy as described with reference to the first embodiment, an endoscope 2, TV camera 4 and image processor 5 are not provided.

As described in the first embodiment, the hand switches 51 (51a to 51d) are freely releaseably connected to respective control devices 53 together with a foot switch 52 and give instructions for selection of the plurality of items of the medical treatment equipment 7 or for operation thereof in prescribed operating modes.

Figure 12:
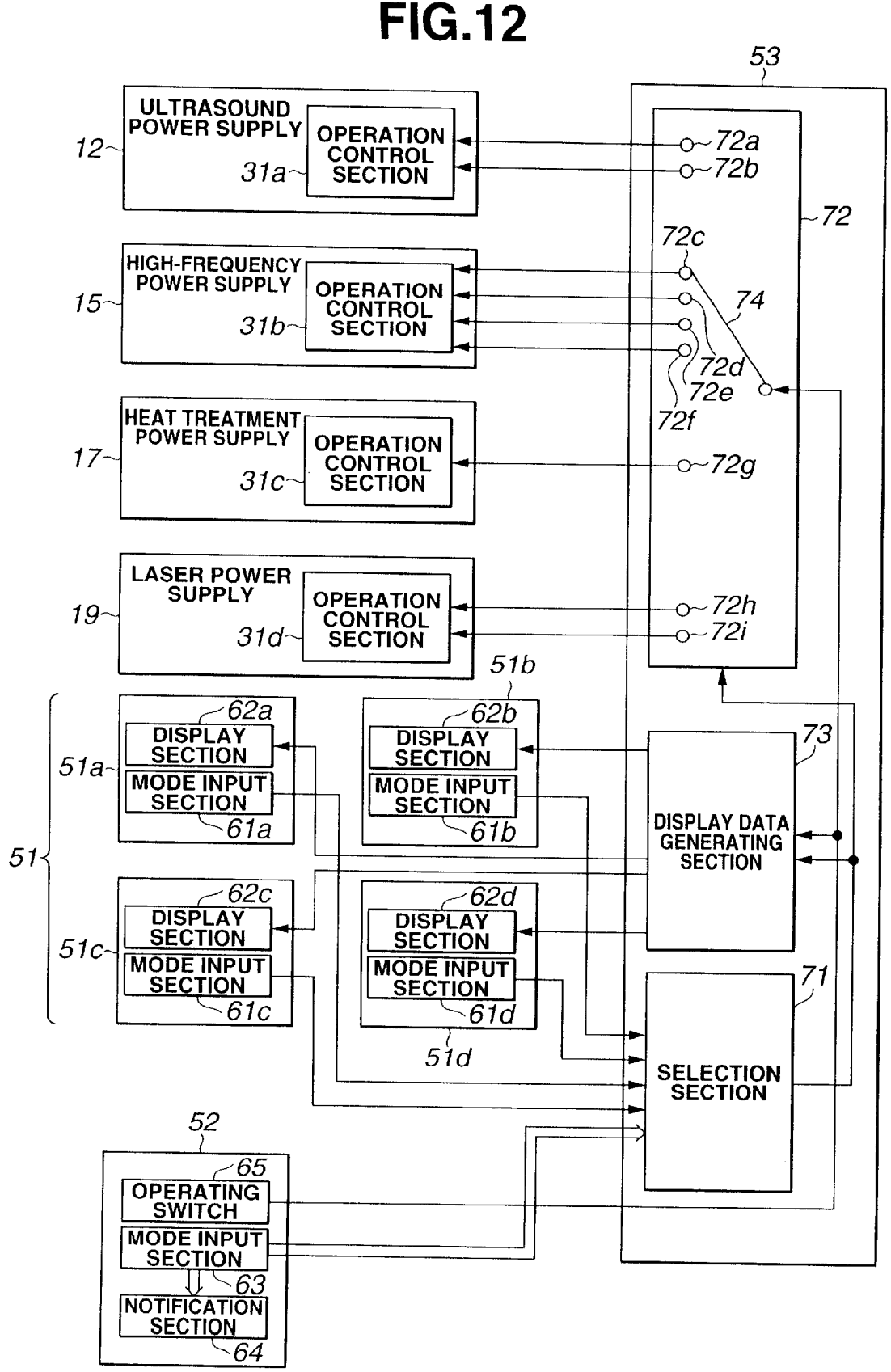
FIG. 12 is a circuit block diagram illustrating the communication connections of the various items of medical treatment equipment of FIG. 11 and the internal layout of the control device.

As shown in FIG. 12, the hand switches 51 (51a to 51d) comprise mode input sections 61a to 61d just like those described with reference to the first embodiment, respectively, and display sections 62a to 62d that display the operating mode of the various items of the medical treatment equipment 7 selected by these mode input sections 61a to 61d are respectively provided.

Also, the foot switch 52 comprises mode input sections 63 that output an operating mode signal to the control device 53 in accordance with the selected operating mode and that output an operating mode alteration signal when the operating mode is altered; a notification section 64 that gives a notification giving notification of the alteration of operating mode when it receives the operating mode alteration signal from a mode input section 63; and a single operating switch 65 like that described in the first embodiment. It should be noted that these mode input sections 63 of the foot switch 52 are also arranged to output the operating mode alteration signal to the control device 53.

The control device 53 comprises a selection section 71 that recognizes the operating mode signal in question by using the operating mode information (operating mode signal or operating mode alteration signal) of the various items of the medical treatment equipment 7 output from the mode input sections 61a to 61d of the hand switches 51 (51a to 51d) or the mode input sections 63 of the foot switch 52 and selects the operating mode of the recognized item of the medical treatment equipment 7 in question; and a switchover section 72 that effects switchover such that the on/off signal from the operating switch 65 of the foot switch 52 is transmitted to the items of the medical treatment equipment 7 selected by this selection section 71; and a display data generating section 73 that generates display data for displaying on display sections 62a to 62d of the hand switches 51 (51a to 51d) arranged on the corresponding items of the medical treatment equipment 7 and whose input signal consists in the operating mode and alteration of operating mode of the items of the medical treatment equipment 7 selected by the selection section 71 or the on/off condition of the operating switch 65 of the foot switch 52.

When an operating mode signal is input from a mode input section 61a to 61d of the hand switches 51 (51a to 51d) or from a mode input section 63 of the foot switch 52, the selection section 71 recognizes this operating mode. The selection section 71 is then arranged to output a selection signal that selects the operating mode in question that has been recognized to the switchover section 72 and the display data generating section 73.

Also, on input thereto of the operating mode signal alteration from a mode input section 63 of the foot switch 52, the selection section 71 ascertains alteration of operating mode from this operation mode alteration signal. Also, the selection section 71 is arranged to output an operating mode cancellation signal to display the data generating section 73.

The switchover section 72 is arranged to output on/off signal from the operating switch 65 of the foot switch 52 to the selected item of the medical treatment equipment 7 through one or other of operating mode contact 72a to 72i with a switch 74 switched over with respect to the operating mode contacts 72a to 72i of the selected items of the medical treatment equipment 7 in accordance with the selection signal from the selection section 71, in the same way as in the first embodiment.

When a selection signal of the selection section 71 is input thereto, the display data generating section 73 is arranged to generate and display display data on one or other of the display sections 62a to 62d of the hand switches 51 (51a to 51d) corresponding to the selected item of the medical treatment equipment 7, in accordance with this selection signal. Also, the display data generating section 73 is arranged to display the on/off condition of the operating mode of the selected item of the medical treatment equipment 7 in accordance with this on/off signal, when the on/off signal is input thereto from the operating switch 65 of the foot switch 52.

Also, the display data generating section 73 is arranged to display the cancelled condition of the operating mode on a display section 62a to 62d of the hand switches 51 in question (51a to 51d) in accordance with this operating mode cancellation signal, when an operating mode cancellation signal of the selection section 71 is input thereto.

The action of the medical treatment system 50 constructed in this way will now be described.

The surgeon sets up the connection condition as in FIG. 11 by connecting the various items of the medical treatment equipment 7 to the control device 53 and turns the devices and the power supply of the devices on. The surgeon then performs treatment on the diseased part of the patient using a desired item of the medical treatment equipment 7.

At this point, it will be assumed for example that the surgeon holds the ultrasound therapeutic instrument 11 on which is mounted the hand switch 51a for the ultrasound therapeutic instrument with one hand or both hands, and performs ultrasound treatment of the diseased part.

The surgeon selects for example the maximum output mode of the ultrasound therapeutic instrument 11 by depressing the mode input section 61a of the hand switch 51a for the ultrasound therapeutic instrument or by covering the mode input section 63 of the foot switch 52 with part of his foot, in the same way as described in the first embodiment.

When this is done, the mode input section 61a of the hand switch 51a for the ultrasound therapeutic instrument or the mode input section 63 of the foot switch 52 makes a selection by detecting the selected operating mode and outputs the maximum output mode signal of the ultrasound therapeutic instrument 11 to the selection section 71 of the control device 53.

The selection section 71 of the control device 53 recognizes the maximum output mode signal from the mode input section 61a of the hand switch 51a for the ultrasound therapeutic instrument or from the mode input section 63 of the foot switch 52. The selection section 71 of the control device 53 thereby selects the maximum output mode of the ultrasound therapeutic instrument 11 and outputs a selection signal to the switchover section 72 of the control device 53 and to display the data generating section 73. The switchover section 72 of the control device 53 switches over the switch 74 to an operating mode contact 72a in accordance with this selection signal.

Also, the display data generating section 73 of the control device 53 generates display data for displaying characters indicating maximum output mode of the selected ultrasound therapeutic instrument 11 on the display section 62a of the hand switch 51a for the ultrasound therapeutic instrument, in accordance with the selection signal from the selection section 71 of the control device 53. The display data generating section 73 of the control device 53 then displays this on the display section 62a of the hand switch 51a for the ultrasound therapeutic instrument as shown in FIG. 13A.

Figures 13A, 13B, 13C:
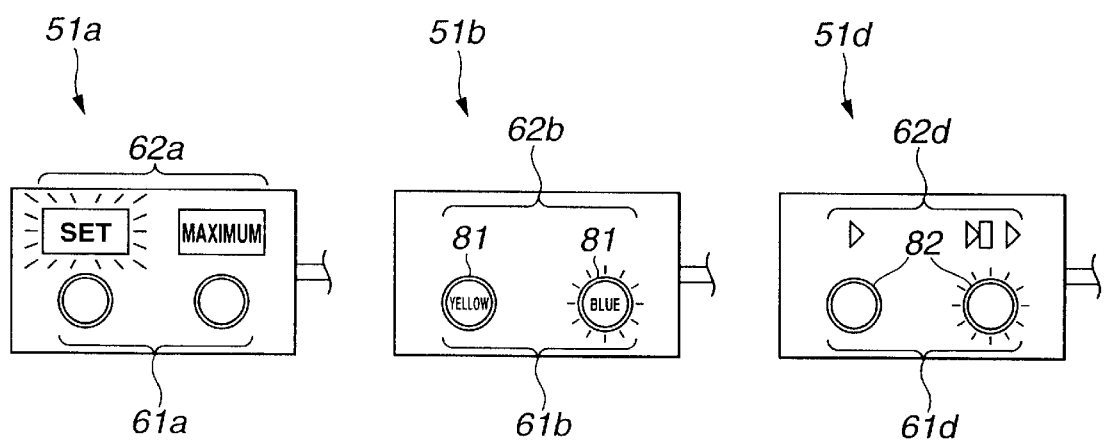
FIG. 13A is an external front view illustrating a hand switch for an ultrasound therapeutic instrument.
FIG. 13B is an external front view illustrating a hand switch for a high frequency therapeutic instrument.
FIG. 13C is an external front view illustrating a hand switch for a laser therapeutic instrument.

As shown in FIG. 13A, the respective operating modes "set" and "maximum" are displayed on the display section 62a of the hand switch 51a for the ultrasound therapeutic instrument and maximum output mode "maximum", which is selected, is flashed.

The surgeon then depresses the operating switch 65 of the foot switch 52 using his/her foot, to commence output of the ultrasound therapeutic instrument 11. When this is done, the operating switch 65 of the foot switch 52 outputs an ON signal to the switchover section 72 and display the data generating section 73 of the control device 53.

The switchover section 72 of the control device 53 outputs the ON signal to the ultrasound power supply 12 through the operating mode contact 72a from the switch 74 which has thus been switched over.

The ultrasound power supply 12 receives an ON signal at the operation control section 31a through the operating mode contact 72a. Drive control of the ultrasound power supply 12 is then performed by the drive control section 31a such that the ultrasound therapeutic instrument 11 is driven in the maximum output mode, in accordance with the ON signal.

Also, in response to the ON signal, the display data generating section 73 of the control device 53 causes display to be effected on the display section 62a of the hand switch 51a for the ultrasound therapeutic instrument with the maximum output mode "maximum" that was made to flash as described above to be illuminated.

Thereupon, the surgeon performs ultrasound treatment with the set output mode by altering the current maximum output mode to the set output mode. The surgeon removes his/her foot from the mode input section 63 representing the current maximum output mode, whilst continuing to press the operating switch 65 of the foot switch 52 with his/her foot.

When this happens, the mode input section 63 of the foot switch 52 outputs an operating mode alteration signal to the notification section 64 and the selection section 71 of the control device 53. The mode input section 63 of the foot switch 52 then outputs the operating mode alteration signal to the notification section 64 and the selection section 71 of the control device 53.

The selection section 71 of the control device 53 ascertains the alteration of operating mode by this operating mode alteration signal and outputs a selection cancellation signal to display the data generating section 73.

In response to the selection cancellation signal, the display data generating section 73 effects display on the display section 62a of the hand switch 51a for the ultrasound therapeutic instrument such that the currently illuminated maximum output mode "maximum" is flashed.

Also, the notification section 64 of the foot switch 52 performs operation to give a notification of the alteration of operating mode by vibration or sound, in response to the operating mode alteration signal.

The surgeon then selects the set output mode by depressing the mode input section 61a representing the set output mode of the hand switch 51a for the ultrasound therapeutic instrument or by covering with part of his/her foot the mode input section 63 representing the set output mode of the foot switch 52.

When this is done, the mode input section 61a of the hand switch 51a for the ultrasound therapeutic instrument or the mode input section 63 of the foot switch 52 outputs the set output mode signal of the ultrasound therapeutic instrument 11 to the selection section 71 of the control device 53.

In response to this set output mode signal, the selection section 71 of the control device 53 selects the set output mode of the ultrasound therapeutic instrument 11 and outputs the selection signal to the switchover section 72 and the display data generating section 73 of the control device 53.

In response to this selection signal, the switchover section 72 of the control device 53 switches over the switch 74 to an operating mode contact 72b.

Also, in response to the selection signal from the selection section 71, the display data generating section 73 of the control device 53 generates display data for displaying characters indicating the set output mode of the selected ultrasound therapeutic instrument 11 on the display section 62a of the hand switch 51a for the ultrasound therapeutic instrument.

The display data generating section 73 of the control device 53 then effects display on the display section 62a of the hand switch 51a for the ultrasound therapeutic instrument such that the set output mode "set" is illuminated. The operation of the control device 53 when ultrasound treatment of the diseased part is terminated or interrupted is the same as in the case of the first embodiment.

Also, the operation of the control device 53 when high frequency treatment of the diseased part is performed is the same as in the case of the ultrasound treatment. The display section 62b of the hand switch 51b for the high-frequency therapeutic instrument is constructed so as to provide color LEDS 81 such as "yellow" or "blue" as a display section to display the operating mode on the switch constituting mode input section 61b, as shown in FIG. 13B. These color LEDS 81 are arranged to flash during selection or during operating mode alteration and to be illuminated during output. In FIG. 13B, the condition is shown in which "blue" of color LEDs 81 representing the coagulation mode is flashed or illuminated.

Also, the operation of the control device 53 when laser treatment of the diseased part is performed is the same as in the case of ultrasound treatment described above. As shown in FIG. 13C, the display section 62d of the hand switch 51d for the laser therapeutic instrument displays the symbol of the operating mode representing continuous mode or intermittent mode. Also, the switch representing the mode input section 61d is provided with white LEDs 82. These white LEDs 82 are arranged to flash during selection or during operating a mode alteration and to be illuminated during output. FIG. 13C illustrates the condition in which the intermittent mode LED of these white LEDs 82 is flashing or illuminated.

As a result, in this medical treatment system 50, display is effected on the therapeutic instrument that is actually being manipulated even in general surgery, thanks to the provision of the hand switches 51 (51*a* to 51*d*) demountably attached on the various therapeutic instruments of the item of the medical treatment equipment 7 with being selected and used. Consequently, in this medical treatment system 50, selection, determination and alteration of operating mode can be achieved without changing the operator's gaze from the therapeutic instrument.

In this way, in the medical treatment system 50 of the second embodiment selection, determination and alteration of operating mode of the medical treatment equipment 7 can be achieved efficiently and without impairing safety and the efficiency of surgical operations thereby improved.

Figure 14:
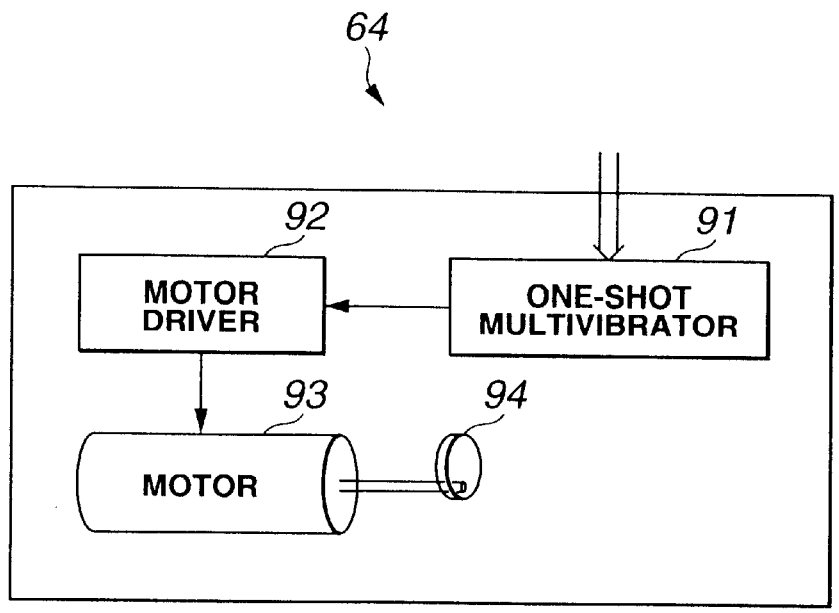
FIG. 14 is a circuit block diagram illustrating the internal layout of a notification section of FIG. 12.

The notification section 64 of the foot switch 52 may be constructed as shown in FIG. 14.

As shown in FIG. 14, the notification section 64 comprises a one-shot multivibrator 91 that generates an ON signal with fixed period on receipt of an operating mode alteration signal from the mode input section 63, a motor driver 92 that is operated on receipt of an ON signal from this one-shot multivibrator 91 and a motor 93 that is driven by this motor driver 92. A reference symbol 94 indicates an eccentric weight arranged at the tip of the shaft of the motor 93.

Thus, with this foot switch 52, by constructing the notification section 64 in this way, the entire foot switch 52 is made to vibrate by this vibration when vibration is generated for a prescribed time on receipt of the operating mode alteration signal from the mode input section 63.

In this way, with this foot switch 52, when the operating mode is altered, even if the display section 62 arranged on the hand switch 51 is in a condition in which it is difficult to view due to manipulation of the therapeutic instruments of the various items of medical treatment equipment 7, alteration of operating mode becomes easy to recognize since the entire foot switch 52 is made to vibrate.

Figure 15:
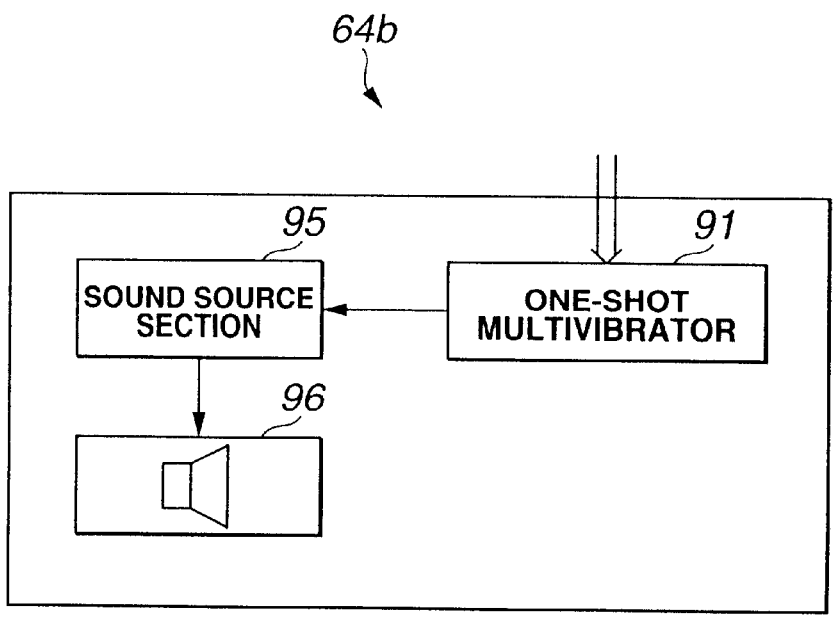
FIG. 15 is a circuit block diagram of a notification section illustrating a modified example of FIG. 14.

Also, the notification section 64 of the foot switch 52 could be constructed as shown in FIG. 15. As shown in FIG. 15, a notification section 64*a* comprises a sound source section 95 that generates a sound source waveform on receipt of an ON signal from the one-shot multivibrator 91 and a speaker 96 that generates sound by means of a sound source waveform of this sound source section 95.

Thus, since the foot switch 52 comprises the notification section 64*b*, it generates sound for a prescribed time on receiving the operation mode alteration signal from the mode input section 63. In this way, with this foot switch 52, when the operating mode is altered, even if the display section 62 arranged on the hand switch 51 is in a condition in which it is difficult to view due to manipulation of the therapeutic instruments of the various items of medical treatment equipment 7, alteration of operating mode becomes easy to recognize since sound is generated from the foot switch 52.

In the present invention, it is clear that a wide range of different embodiments can be constituted based on the present invention without departing from the spirit and scope of the invention. The present invention is restricted by the appended claims but otherwise is not restricted by these specific embodiments.

What is claimed is:

1. A medical treatment system having medical treatment equipment and a control device that controls the operation of this medical treatment equipment, comprising:

an operation control section that controls operation of a therapeutic instrument connected to said medical treatment equipment with respect to a selected single function thereof;

a selection switchover section provided in said control device and that selects a single function in a therapeutic instrument by controlling said operation control section;

a selection input section that selectively inputs a single function in a therapeutic instrument by activating said selection switchover section by selection of the prescribed input section from among input sections arranged corresponding to the number of functions possessed by said therapeutic instrument; and an operating switch that outputs operation instructions in respect of a single function in the therapeutic instrument selected by said selective input section to said selection switchover section.

2. The medical treatment system according to claim 1 wherein, when there are a plurality of said items of the medical treatment equipment, said selection switchover section selects a prescribed item of the medical treatment equipment selected by said selection input section from among said plurality of items of the medical treatment equipment and in addition selects one function in the therapeutic instrument.

3. The medical treatment system according to claim 1 wherein said control device comprises a display data generating section that generates display data for giving a notification in respect of a single function in the selected therapeutic instrument, in accordance with the selection result of said selection switchover section and causes display data generated by this display data generating section to be displayed in the display section.

4. The medical treatment system according to claim 3 wherein each single function in the therapeutic instrument displayed in said display section is displayed at different positions depending on the selection result of said selection input section or the selection result of said selection switchover section.

5. The medical treatment system according to claim 3 wherein each single function in the therapeutic instrument displayed in said display section is displayed in different colors depending on the selection result of said selection input section or the selection result of said selection switchover section.

6. The medical treatment system according to claim 3 wherein said selection input section outputs an alteration signal when alteration of a single function in the therapeutic instrument that is currently being driven and controlled is detected.

7. The medical treatment system according to claim 6 wherein said selection switchover section outputs a cancellation signal for canceling a single function in the therapeutic instrument that is currently being driven and controlled in response to the alteration signal from said selection input section to said display data generating section; and said display data generating section causes the cancellation condition of the single function in the therapeutic instrument that is currently being driven and controlled to be displayed in said display section in response to the cancellation signal of said selection switchover section.

8. The medical treatment system according to claim 6 comprising a notification section for giving a notification of this alteration of function in response to the alteration signal from said selection input section.

9. The medical treatment system according to claim 8 wherein said notification section generates vibration synchronized with the function alteration detected by said selection input section.

10. The medical treatment system according to claim 8 wherein said notification section generates sound synchronized with the function alteration detected by said selection input section.

11. A medical treatment system having medical treatment equipment and a control device that controls the operation of this medical treatment equipment, comprising:

an operation control section that controls operation of a therapeutic instrument connected to said medical treatment equipment with respect to a selected single function thereof;

a selection switchover section provided in said control device and that selects a single function in a therapeutic instrument by controlling said operation control section;

a selection input section that selectively inputs a single function in a therapeutic instrument by activating said selection switchover section by selection of the prescribed input section from among input sections arranged corresponding to the number of functions possessed by said treatment implement;

a switchover section that, when there is a plurality of items of said medical treatment equipment, selects a corresponding item of the medical treatment equipment from among said plurality of items of medical treatment equipment in accordance with a single function in the therapeutic instrument selected by said selection switchover section and an operating switch that outputs operation instructions in respect of a single function in the therapeutic instrument selected by said selective input section to said selection switchover section.

12. The medical treatment system according to claim 11 wherein said control device comprises a display data generating section that generates display data for giving a notification in respect of a single function in the therapeutic instrument of the selected item of the medical treatment equipment, in accordance with the selection result of said selection switchover section, and causes display data generated by this display data generating section to be displayed in the display section.

13. The medical treatment system according to claim 12 wherein each single function in the therapeutic instrument of the item of the medical treatment equipment displayed in said display section is displayed at different positions depending on the selection result of said selection input section or the selection result of said selection switchover section.

14. The medical treatment system according to claim 12 wherein each single function in the treatment implement of the item of the medical treatment equipment displayed in said display section is displayed in different colors depending on the selection result of said selection input section or the selection result of said selection switchover section.

15. The medical treatment system according to claim 12 wherein said selection input section outputs an alteration signal when alteration of a single function in the therapeutic instrument that is currently being driven and controlled is detected.

16. The medical treatment system according to claim 15 wherein said selection switchover section outputs a cancellation signal for canceling a single function in the therapeutic instrument that is currently being driven and controlled in response to the alteration signal from said selection input section to said display data generating section; and said display data generating section causes the cancellation condition of the single function in the therapeutic instrument that is currently being driven and controlled to be displayed in said display section in response to the cancellation signal of said selection switchover section.

17. The medical treatment system according to claim 15 comprising a notification section for giving a notification of this alteration of function in response to the alteration signal from said selection input section.

18. The medical treatment system according to claim 17 wherein said notification section generates vibration synchronized with the function alteration detected by said selection input section.

19. The medical treatment system according to claim 17 wherein said notification section generates sound synchronized with the function alteration detected by said selection input section.

* * * * *